(12) United States Patent
Löfgren et al.

(10) Patent No.: US 8,075,490 B2
(45) Date of Patent: Dec. 13, 2011

(54) VASCULAR RESISTANCE GAUGE

(75) Inventors: Mikael Löfgren, Mölndal (SE); Mikael Charlez, Mölndal (SE)

(73) Assignee: Assut Europe S.p.A., Roma (IT)

( * ) Notice: Subject to any disclaimer, the term of this patent is extended or adjusted under 35 U.S.C. 154(b) by 1481 days.

(21) Appl. No.: 11/467,172

(22) Filed: Aug. 25, 2006

(65) Prior Publication Data

US 2007/0060820 A1   Mar. 15, 2007

Related U.S. Application Data

(60) Provisional application No. 60/596,030, filed on Aug. 25, 2005.

(30) Foreign Application Priority Data

Aug. 25, 2005  (SE) ...................................... 0501889

(51) Int. Cl.
*A61B 5/02*    (2006.01)
*A61M 5/00*    (2006.01)

(52) U.S. Cl. ........................................ 600/481; 604/187
(58) Field of Classification Search .................. 128/898; 600/481; 604/187

See application file for complete search history.

(56) References Cited

U.S. PATENT DOCUMENTS

2003/0050556 A1\*   3/2003   Uber et al. .................... 600/420

FOREIGN PATENT DOCUMENTS

WO         9612438 A1    5/1996

\* cited by examiner

*Primary Examiner* — Patricia Mallari
*Assistant Examiner* — Christian Jang
(74) *Attorney, Agent, or Firm* — Renner, Otto, Boisselle & Sklar, LLP

(57) ABSTRACT

A system and a method for assessing the patency of a vessel or a graft during coronary artery bypass grafting surgery or PTCA, said system comprising a syringe capable of electronically measuring the pressure and flow of a fluid that is injected into the vessel or graft. The system also comprises a reading device connected to said syringe for displaying flow, pressure and flow resistance parameters.

13 Claims, 6 Drawing Sheets

VASCULAR RESISTANCE GAUGE

FIELD OF INVENTION

The present invention refers to methods and appliances for use at heart surgery. Specifically, the invention refers to methods and a device for assessing flow resistance parameters of graft and native vascular bed during coronary artery bypass grafting surgery and PTCA.

BACKGROUND

Approximately one third of all deaths in the affluent society of the western world result from coronary artery disease, and almost all elderly persons have at least some impairment of the coronary artery circulation. For this reason, the normal and pathological physiology of the coronary circulation is one of the most important subjects in the entire field of medicine.

One way of treating coronary artery disease is by coronary artery bypass grafting, which is surgery where vessel grafts are used to bypass one or more stenoses (constrictions) in the coronary arteries.

The success of a bypass grafting surgery operation depends on several factors, including the quality of the graft(s), the position of the graft(s) and methods for assessing the quality of a graft and methods for assessing the possible contribution of a graft to the arterial blood supply of the myocardium.

Most current methods for increasing the benefits of a bypass grafting surgery operation are of manual nature, relying on skill and experience of the surgeon. There seems to be few methods and devices for assessing the absolute quality of a graft and related matters in an objective and numerically presentable manner.

Thus, there is a need for a method and a device for assessing graft quality, making it possible to further increase beneficial outcome of coronary artery bypass grafting surgery.

Descriptions of coronary anatomy can be found in a textbook or atlas, e.g. Arthur C Guyton 1991, Textbook of medical physiology, eight edition, W.B. Saunders Company, Harcourt Bruce Jovanich Inc., London, page 234-244.

Background of certain medical terms used in this document can be found in the following articles: "Competitive flow", A technique for evaluating competitive flow for intraoperative decision making in coronary artery surgery, Gil Bolotin et al, Ann Thorac Surg 2003; 76:2118-2120; Does competitive flow reduce internal thoracic artery graft patency?, Sabik J F 3$^{rd}$ et al., Ann Thorac Surg 2003 November; 76(5):1490-7; "Run off quality", Prospective evaluation of coronary arteries: influence on operative risk in coronary artery surgery, H. Corbineau et al, Eur J Cardiothorac Surg 199; 16:429-434; "Flow resistance", Intraoperative assessment of coronary flow and coronary vascular resistance during coronary bypass surgery, Scan Cardiovasc J. 199; 33(1): 23-8.

Ischemic Heart Disease

Ischemic heart disease is a term for heart-related conditions caused by poor delivery of blood that carries oxygen to the heart. It is most commonly caused by blockages in the coronary arteries, the blood vessels that provide blood to the heart muscle itself. Ischemic heart disease is also known as coronary heart disease and coronary artery disease, and includes heart attack and angina (chest pain or discomfort). Heart disease usually develops over time as cholesterol and fat build up on the inside of the heart's arteries, narrowing the space through which blood flows. Chest pain or discomfort, also called angina, may occur when not enough blood reaches the heart. A heart attack occurs when a part of the heart dies because the blood supply was blocked and there was not enough oxygen to keep it alive.

Surgical Treatment of Coronary Disease

In many patients with coronary ischemia, the constricted areas of the coronary vessels are located at only a few discrete points, and the coronary vessels beyond these points are normal or almost normal. A surgical procedure has been developed in the past 25 years, called aortic coronary bypass (CABG), for anastomosing small vein grafts to the aorta and to the sides of the more peripheral coronary vessels. Usually, one to five such grafts are performed during the operation, each of which supplies a peripheral coronary artery beyond a block. The vein that is used for the graft is usually the long superficial saphenous vein removed from the leg of the patient. The acute results from this type of surgery have been especially good, causing this to be the most common cardiac operation performed. Anginal pain is relieved in most patients. Also in patients whose hearts have not become too severely damaged prior to the operation, the coronary bypass procedure often can provide the patient with normal survival expectation.

PRIOR ART

WO 96/12438 discloses a method and a system for measuring the flow rate of a liquid through a blood vessel to be used as graft on a patient in need thereof, where a certain quantity of this fluid is passed under controlled conditions through the vessel, thus establishing whether it is suitable for use as graft. The system comprises a large syringe connected to a motor controlled pump creating exactly defined conditions, and means for calculating the flow rate and whether the vessel is suitable for intended patient.

SUMMARY OF THE INVENTION

The present invention refers to a system suitable for assessing vascular graft patency, the system comprises a syringe for injecting a fluid into said vascular graft and the system also comprises means for determining the flow rate and pressure of said fluid. The syringe is devised to be manually operated and means are arranged confined within an outer border of said syringe to measure pressure and flow resulting from manual depression of a syringe piston.

The system may comprise means for electronically sensing the pressure of the fluid in the syringe and means for electrically or magnetically determining the rate of movement of a piston part of the syringe relative to a housing of said syringe said rate of movement giving rise to a flow proportional to said movement.

The system may also comprise a pressure sensor, arranged at the piston part of the syringe and communicating with the pressure in the fluid of the syringe through a pressure channel, a first end of the pressure channel is arranged at the piston, being exposed to the pressure of the fluid in the syringe, the first end of the channel may be protected by a flexible membrane; the second end of the pressure channel 422 connects to the pressure sensor 424.

A syringe where a magnetic tape, having areas of different magnetism alternating in its longitudinal direction, is attached to either the piston part or the housing of the syringe, and where two magnetic sensors are arranged on the other part of the syringe having a distance between the sensors that is not a multiple of the distance between two magnetic areas of said tape.

The system where the position of the piston is sensed by a capacitive circuit and where the housing of the syringe is provided with conductive areas attached to the syringe housing and where also the piston part of said syringe is provided with conductive areas in such a way that when the piston part of said syringe is pressed into the housing of said syringe the capacitance of an electrical circuit comprising said conductive areas is changed.

The system may also comprise that a stationary part of a potentiometer is attached to the syringe housing and a mobile part of said potentiometer is attached to the piston part of said syringe, or vice versa.

A reading device for use with a syringe, comprising at least one inlet for signals representative of said position and said pressure, and further comprising a display and means for converting signals representative of said position to a flow value, and means to compute a vascular resistance value from said pressure and position signals. Means are arranged, preferably at the piston part, for wirelessly transmitting signals representative of said position, pressure and resistance to a remote unit.

A system for inter-operatively assessing vascular resistance, comprising the system and the reading device, and a tube for connecting the syringe to the vessel in question, and a cable for connecting one or more sensors of the syringe to the reading device.

A method for measuring free graft patency during surgery, comprising the following steps:
  Providing the graft, e.g. by taking out vena saphena magna from one leg of the patient.
  Preparing the vein for becoming a graft according to standard procedures,
  Connecting a first end of the vein, the end that will become the proximal end of the final anastomosis, to the tubing of the syringe of the vascular resistance gauge.
  Injecting a fluid through the graft by manually pressing the piston part of the syringe, thereby creating a flow through the graft and a pressure in the syringe.
  Reading the vascular resistance of the graft on the display of the reading device.

A method for measuring vascular resistance of coronary vessels of a beating or arrested heart during open heart surgery, comprising the following steps:
  Opening chest and expose the heart according to standard procedures.
  Identify the coronary artery of interest.
  Identify point of interest, i.e. the point on the coronary artery of interest, where the graft is to be connected/sutured.
  On the beating heart, make an incision at the point of interest and, if necessary, take measures to avoid unnecessary bleeding.
  Connect the coronary artery of interest, at the point of interest, to the tubing of syringe of the vascular resistance gauge.
  Inject a fluid into the coronary artery of interest, at the point of interest, by manually pressing the piston part of the syringe, thereby creating a flow through the graft and a pressure in the syringe. The injection is preferably continued during at least three heart beats, enabling calculation of a good average resistance.
  Read the average resistance of the coronary vascular bed of interest on the display of the reading device.

DETAILED DESCRIPTION OF THE PREFERRED EMBODIMENTS

Definitions

Figure 1:
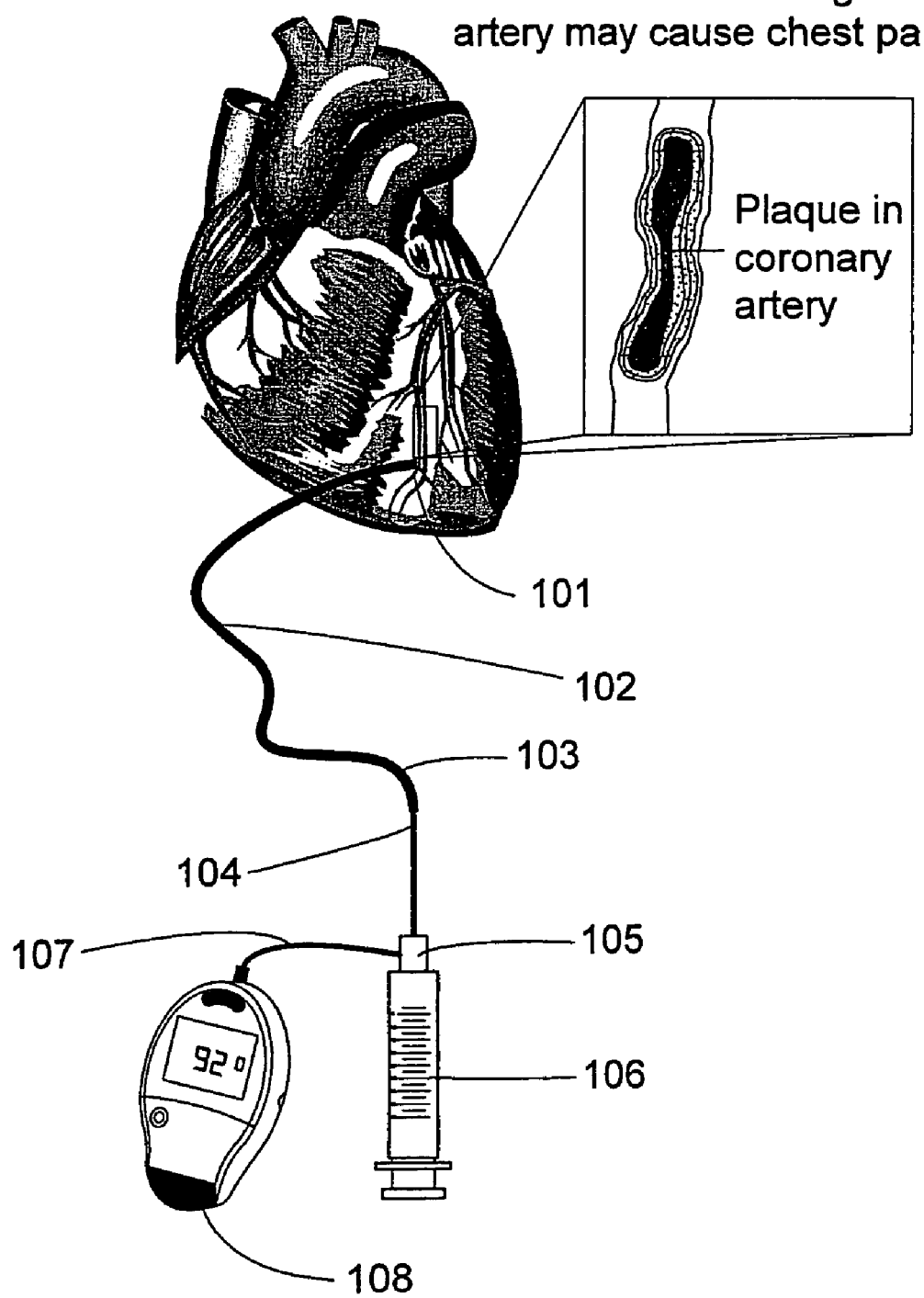
FIG. 1 shows a schematic overview of a setup for assessing vascular resistance for a vein graft.

As used herein the following terms refer to the following:
Myocardial Flow and Coronary Flow Reserve
  Myocardial Flow (Qmyo) is the flow passing through the myocardium. The myocardium has a certain amount of flow resistance Rmyo during systole/diastole. The ability to increase coronary blood flow in response to vasoactive mechanisms is coronary flow reserve. If Qmyo increases and Rmyo decreases on the arrested heart, it indicates a certain coronary flow reserve.
Coronary Vascular Resistance
  The measurement of coronary vascular resistance on the arrested heart (zero cardiac work) reveals an early warning on grafts and coronary beds at potential high risk for inadequate perfusion. A surgeon can perform immediate revision and ensure graft patency
Competitive Flow and Graft Patency
  The influence of the competitive flow on graft flow depends on the magnitude of the resistances Rcoron and Rgraft. Rcoron is largely a function of the severity of the stenosis; Rgraft includes factors such as graft length and size, vasospasm, and technical errors. Competitive flow is indicated off pump by an increase in mean flow when the native coronary artery is occluded and hence indicated on pump by a decrease in mean flow when the native coronary artery is occluded. Graft flow, during native coronary artery occlusion, conclusively demonstrates graft patency.
Graft Control
  The physiology in cardiovascular surgery is complicated by the fact that postoperative flow in saphenous vein grafts is different than flow in mammary and other arterial conduits. Graft control refers to the activity of revealing an early flow and resistance impairment on the harvested saphenous graft material before the anastomosis procedure
Stent Control
  Stent control is the fraction between the values of post and prestenotic pressure, flow and resistance. The fraction gives the percentage of the pressure, flow and resistance through the stenosis related to the flow as measured immediately after the stenosis. Intravascular pressure, flow and resistance measurement by stent control is also valuable after treatment in order to determine whether or not the intervention has been successful. Stent control refer to the activity of measuring flow improvements due to stent implantation.
Arrested Heart
  An arrested heart is a non-beating living heart, cooled down to approximately 15° C. and which is being kept non-beating and at said temperature by the aid of so called cardioplegia-solution.

Referring now to FIGS. 1 and 2a-2d, a system for assessing vascular graft patency includes a syringe for injecting a fluid into the vascular graft, sensors for determining fluid flow characteristics such as pressure and flow rate of the fluid that is injected into the vascular graft by the syringe, and a display for displaying calculated fluid flow characteristics and/or graft patency characteristics to a user, so that the patency of the graft may be assessed during surgery to implant the graft. The system provides quick and easy intraoperative assessment of coronary vascular flow resistance including assessment of graft flow resistance. The syringe may be operable by a surgeon or nurse.

During surgery, the syringe is connected to the coronary bypass graft and a fluid, such as saline or a special solution, such as a cardioplegia solution, is injected in the graft. Vascular resistance is calculated from flow and pressure by the aid of Poiseuille-Hagen equation, or other fluid mechanics equations, which have been incorporated in the reading device software. The results are displayed, and the surgeon can use them to make decisions on further actions.

The flow sensor of the syringe provides for accurate measurements of the injected volume of fluid by means of sensing the position of a piston of said syringe relatively to a housing of the syringe. The position is sensed by means of a linear potentiometer, connected to the piston. The position of the piston may alternatively be sensed magnetically by means of magnetic areas arranged in certain ways, and magnetic sensors arranged to sense the presence and movement of the areas.

In another embodiment, the means for determining the flow rate of said fluid that is injected into said graft may be determined by a venturi meter.

FIG. 1 shows a schematic overview of a setup for assessing the vascular resistance of a vein graft 102 used in coronary artery bypass grafting (CABG) surgery. A syringe 106 is provided with a sensor 105 for providing a signal, representative of a pressure of a fluid inside the syringe. The syringe comprises a piston and a syringe housing. The syringe also comprises a sensor providing a signal representative of a position of said piston relative to said housing.

A tube 104 is arranged to connect the syringe 106 to a proximal end 103 of the vein graft 102. A distal end of the graft 102 has been connected to the coronary circulation during a first part of a coronary artery bypass graft surgery operation.

A connection cable 107 is connecting the sensors of the syringe with a reading device 108. The reading device 108 is arranged to be able to present flow, pressure and cardiovascular resistance. The reading device is also arranged to be able to perform real time measuring and logging of data.

Figure 2A:
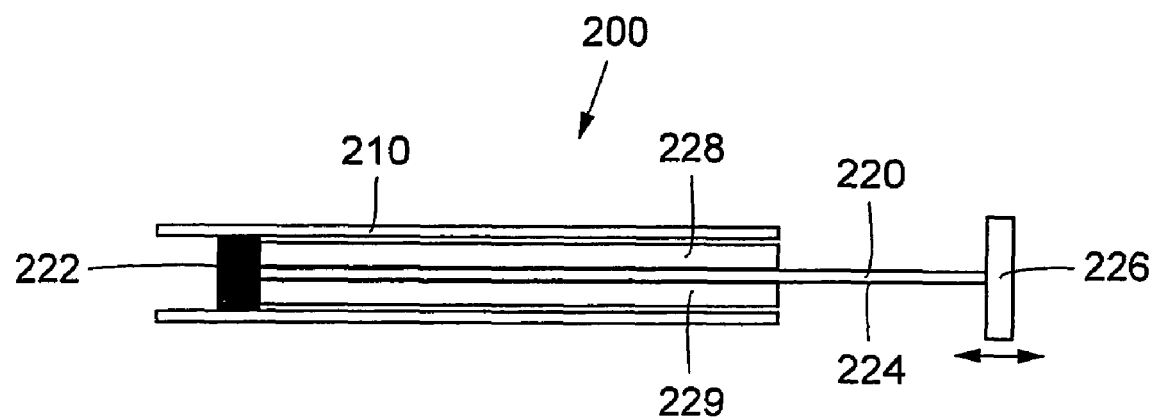
FIG. 2a-d show different embodiments of a syringe with detection means for detecting movement of a piston part relatively to a housing of said syringe by means of magnetism.

FIG. 2a shows schematically two parts of a syringe 200; a housing 210 and a piston part 220, which part 220 is movable inside said housing 210.

The piston part 220 comprises a piston 222, the piston 222 is attached to a first end of a rod 224, the rod 224 is at a second end formed as a push-button 226.

The piston part 220 is further provided with one or more longitudinal supports 228, 229.

Figure 2B:
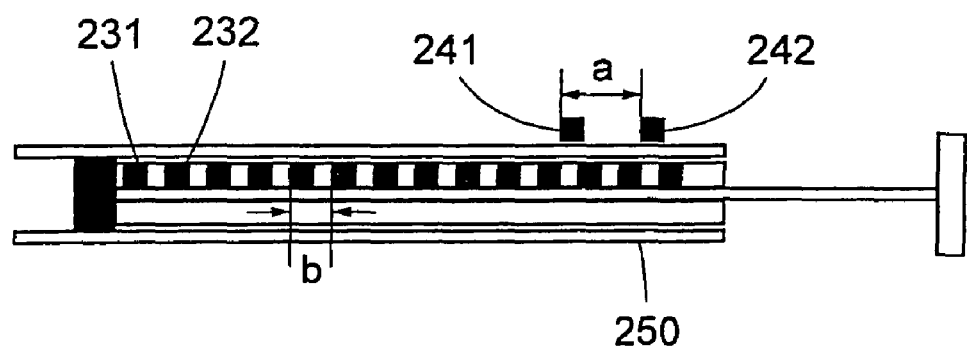

Referring to FIG. 2b, one of the supports 228 is provided with magnetic tape, having a number of magnetic areas 231, 232 of ferrite material having relatively large hard-magnetic properties. Areas 231, 232 of the ferrite material are alternated with non-magnetic areas. A first 241 and a second 242 magnetic sensor is arranged at a close end 250 of the housing 210. The magnetic sensors 241, 242 are arranged to detect the magnetic areas 231, 232. The two sensors 241, 242 are positioned having a distance a between them. Said distance a between the sensors 241, 242 are different from a distance b between two adjacent magnetic sections 231, 232.

In other embodiments, the magnetic tape may be encoded with absolute position information that may be read by a traditional magnetic tape read head. Embodiments with magnetic tape may generally have higher resolution.

A possible value of distance b is 2 mm. A resolution of the mechanism is better than 2 mm, due to the use of two sensors 241, 242 and computer processing of the signals from the two sensors. Computer processing is provided in the reading device 108 (not shown in FIG. 2b)

When the movable piston part 220 is pushed into the syringe housing 210, the magnetic areas will move in the vicinity of the sensors 241, 242, which movement will result in variations in the output signal from said sensors 241, 242.

The distance a between the sensors 241, 242 and the distance b between the magnetic areas are known, and distance a is arranged not to be a multiple of distance b. This fact makes it possible to calculate the linear movement of the piston part 220 from the signals from the sensors 241, 242. In alternate embodiments the sensors can be Hall sensors or magnetoresistive sensors. Magnetic sensors are available from many companies (Philips, Honeywell, Allegro etc.). Magnetic tapes can be purchased from e.g. 3M and Arnoldmagnetics. The magnetic tape can be arranged on the piston part and the sensors on the housing or vice versa.

The direction of magnetisation is arranged suitably. In the embodiments described above no calibration is necessary, because it is a time between two signal events that is detected. The magnetic areas may also preferably be arranged as area of alternating direction of magnetisation, i.e. NNN SSS NNN SSS NNN SSS, etc.

Permanent Magnets

Figure 2C:
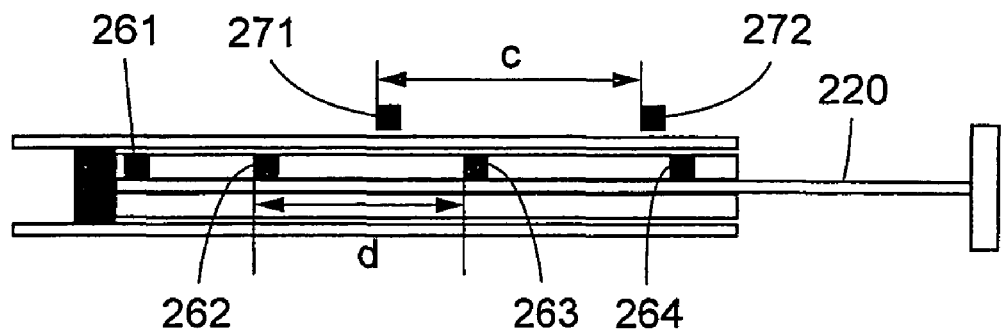

Referring to FIG. 2c, the piston part 220 of the syringe 200 may be provided with a moderate number, i.e. three or four hard-magnetic magnets 261-264, e.g. permanent magnets of e.g. NdFeB alloy. Hall sensors 271, 272 are attached to the syringe housing 210 to sense the magnetic field from magnets 261-264. The strength and nature of the magnetic field at the position where the sensors 271, 272 are arranged depend on the positions of the permanent magnets 261-264, and due to this the position of the piston part 220 relatively to the housing 210 can be determined.

The syringe signal strength may be calibrated to improve the calculation of the value of the movement of the piston part 220. The syringe sensors may be formed from many of the large number of permanent magnets on the market, having different geometries and dimensions and directions of magnetization. As mentioned above it is also possible to arrange the permanent magnets on the housing and the sensors on the moving part, i.e. the piston part 220. However, when having magnets on the housing, it is then necessary to consider the risk that the magnets would attract magnetic material in the vicinity.

Magnetic Ink

Figure 2D:
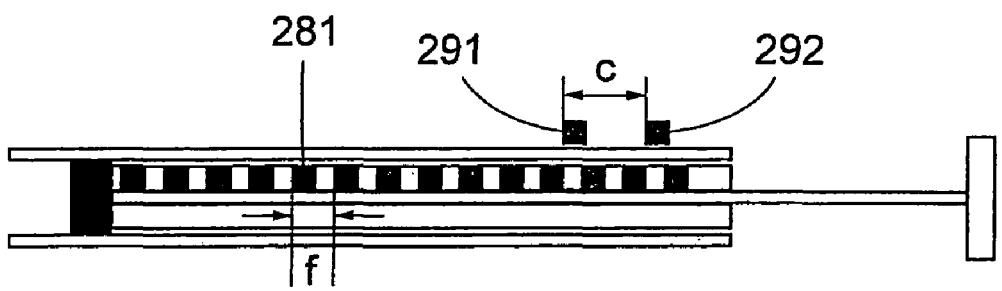

Referring to FIG. 2d, magnetic areas or magnetic sections may be printed in any desired pattern using magnetic ink, e.g. written by an ink-jet printer on the housing or on the piston part 220. In the case the magnetic ink has soft magnetic character, i.e. no magnetic remanence, inductive sensors are used which detect the presence of the magnetic ink. The same method and type of data processing of the output signals are used as for the magnetic tape. Inductive sensors 291, 292 excite the magnetic ink 281 and detect the presence of the magnetic areas 281. Use of inductive sensors 291, 292 may give higher resolution in velocity of the moving piston part. It is also possible to arrange the magnetic areas with magnetic remanence.

Position Sensing by Means of Potentiometer

The position of the piston may be sensed by a linear potentiometer. The stationary part of the potentiometer may be attached to the syringe housing and the mobile part of the potentiometer to the piston part of the syringe. In an alternative embodiment the stationary part is attached to the piston and the mobile part to the housing. This may be advantageous in that a resistance track more easily can be fitted on the piston part without increasing a diameter of the syringe.

Position Sensing by Means of Capacitive Sensor.

The position of the piston may be sensed by a capacitive circuit where the housing of the syringe is provided with conductive areas attached to the syringe housing and where also the piston part of the syringe is provided with conductive areas in such a way that when the piston part of the syringe is pressed into the housing of the syringe the capacitance of an electrical circuit comprising the conductive areas is changed. The change of the capacitance is used as a measure of the movement of the piston part relatively to the housing.

Venturi Meter

Figure 3:
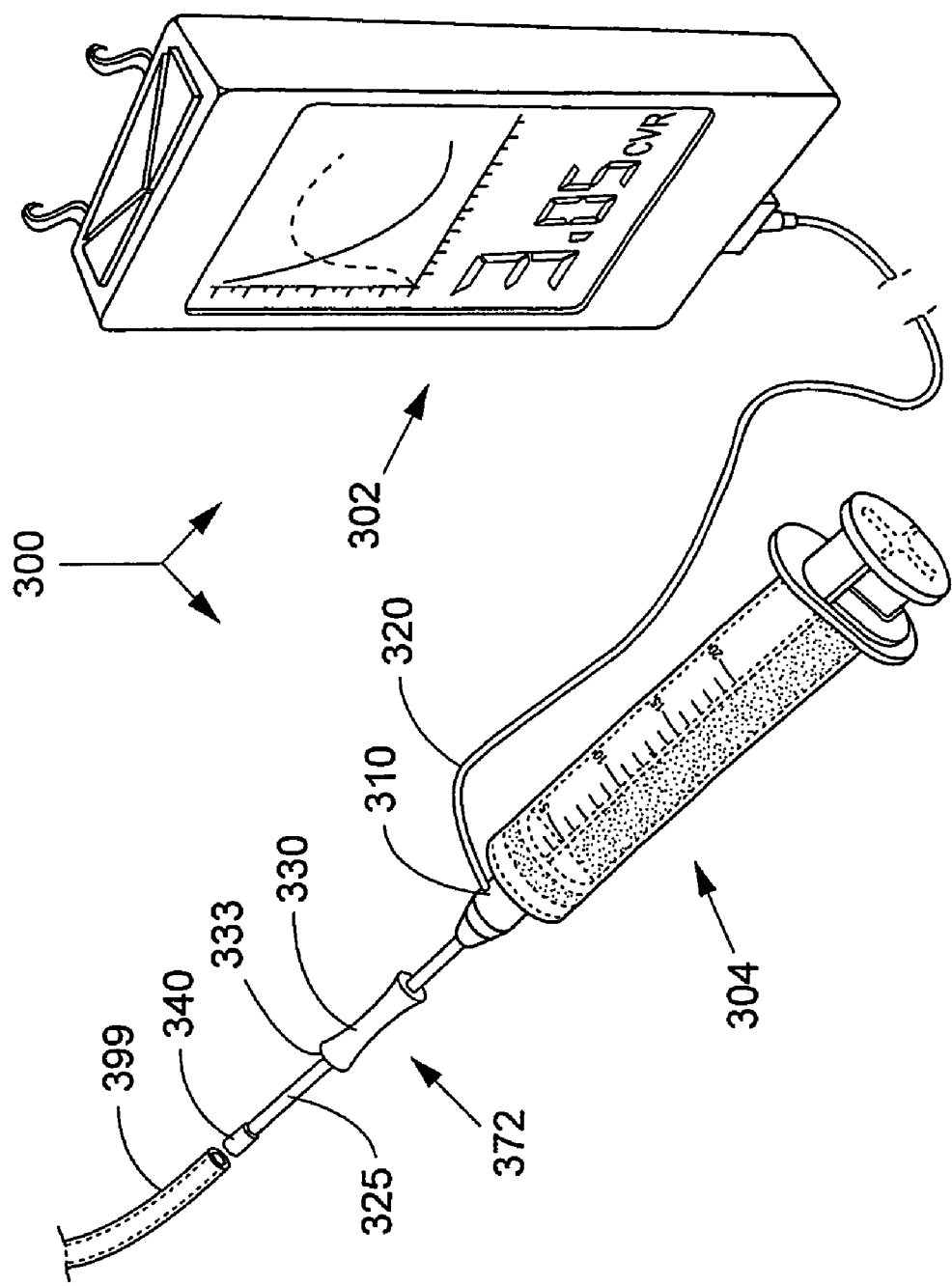
FIG. 3 shows another embodiment of a system for assessing vascular resistance

Referring to FIG. 3, a system 300 for assessing vascular flow resistance may include a syringe 304, a reading device 302, a cable 320 from the syringe 304 to the reading device 302. The system may also be provided with a venturi flow meter 310 comprising pressure sensors positioned at proper locations at or near a nozzle section and an expanding section of the venturi flow meter. The pressure sensors are connected to the reading device 302 by means of the cable 320.

Quick Coupling

FIG. 3 also shows a quick coupling 330, 340 for connecting a tube 325 of the syringe 304 to the graft vessel 399. The quick coupling 330, 340 comprises a bulb part 340 and a funnel part 330. Said funnel part 330 comprises a tapering inside diameter with a big end 333 facing the bulb part 340. When connecting the syringe 304 to the graft vessel 399, the bulb part is inserted in the vessel 399. The funnel part 330 is subsequently slid over the tube 325 towards the bulb part 340 such that the graft wall of the graft vessel 399 becomes squeezed between the inside of said funnel part 330 and the outside of said bulb part 340. The outside diameter of said bulb part is smaller than the inside average diameter of said funnel part. At a certain point of the funnel part the inside diameter is approximately equal to the sum of the outer diameter of the bulb part 340 and the graft vessel wall thickness times two. The funnel part 330 is provided with a bore for the tube 325 such the said funnel part 330 is slideable over said tube 325. The bulb part is provided with a bore to let liquid flow from the tube 325 through said bore. In one embodiment the funnel part is provided with a grip 332 comprising a central tapering 332.

Reading Device

Referring to FIG. 3, the system 300 for assessing vascular flow also comprises a reading device. The reading device is connected to sensors, sensing the pressure in the fluid leaving the syringe 304, and also sensing the movement of the piston, masking it possible to calculate a resistance experienced by the syringe when trying to expel its content.

The reading device comprises hardware and/or software, capable of:

Reading a signal from the pressure sensor representative of the pressure in the fluid in the syringe.

Reading a signal representative of either a position of the piston of the syringe, or a signal representative of the movement or rate of movement of said piston.

Converting the read signal representative of the pressure in the fluid in the syringe to a pressure value p, representative of said pressure.

Converting the read signal representative of the position or movement of the piston to a flow value .phi. representative of a fluid flow from the syringe.

Calculating an experienced resistance R to the expelled flow as the quotient between the pressure and the flow:

$$R = P/\phi \qquad (1)$$

Presenting the resistance value R, the pressure P and the flow ø on a display.

Calculating, presenting and keeping track of maximum and minimum resistance during a time period corresponding to the time the piston part was pressed the last time. Said resistance being calculated by selectively using either peak pressure together with coincident flow for systolic resistance, or low pressure together with its coincident flow for diastolic resistance.

Pressure Sensing

Figure 4:
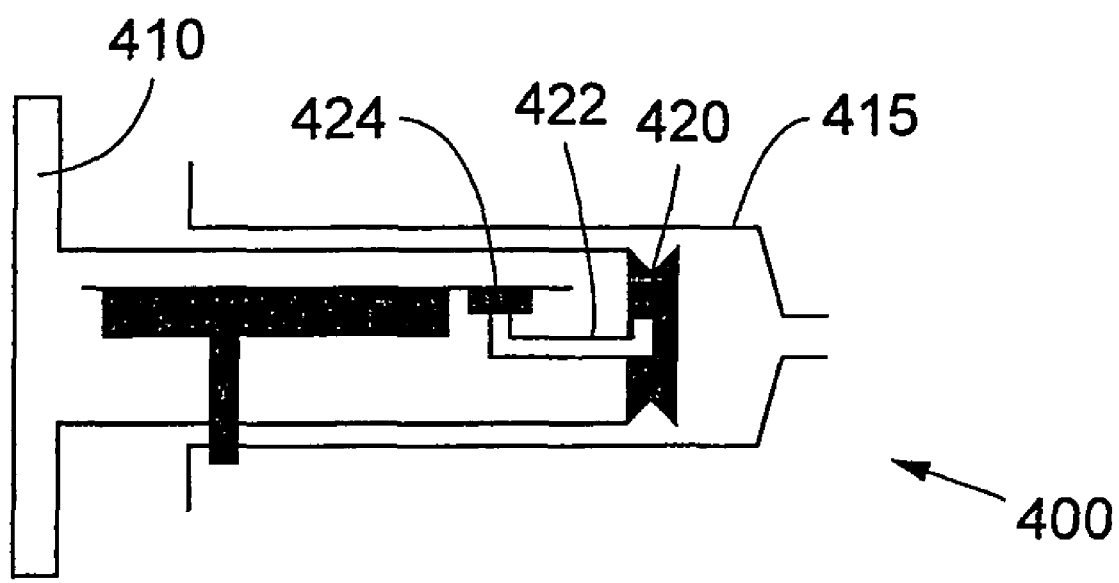
FIG. 4 schematically shows a syringe with a pressure channel.

FIG. 4 schematically shows the syringe 400 with the piston part 410 and the housing 415. The piston part is provided with a piston 420. Under a flexible membrane in the piston 420 is a fixed end of a pressure channel 422. The pressure channel is connected to and has a second end at a pressure sensor 424. The pressure sensor 424 and the pressure channel 422 are arranged at the piston part and move together with said part. This gives the advantage of having all of the electronics attached to only one part of the syringe.

Figures 5A, 5B:
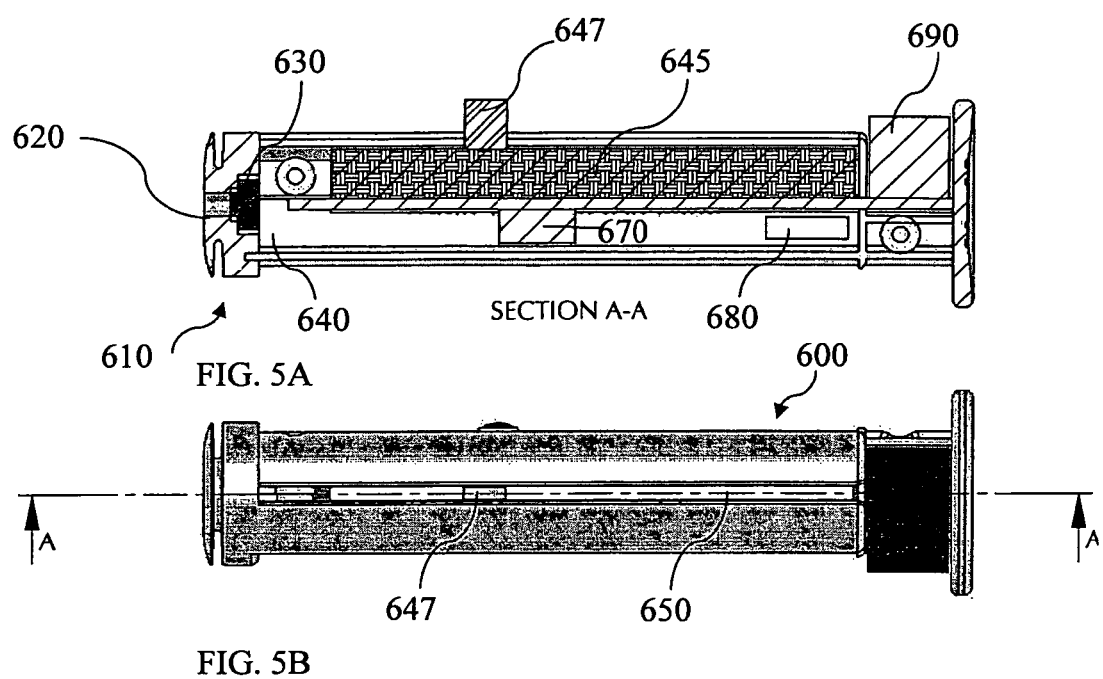
FIGS. 5a and 5b show a hollow syringe piston stem according to an alternate embodiment.

FIGS. 5a and b shows a hollow piston stem 600 according to another embodiment of the invention. The hollow piston stem 600 is provided with a piston portion 610 at its farther end comprising means for movably sealing against the inside of a syringe housing. The piston portion is provided with a bore 620 arranged to provide a first cavity 620 in front of a first pressure sensitive surface of a pressure sensor 630 and to connect this cavity to the pressure of a fluid in the syringe. The pressure sensor is arranged such that a second pressure sensitive surface of said pressure sensor 630 is subjected to the pressure in a second cavity 640 arranged to be in connection with the surrounding atmospheric pressure. The pressure sensor is sealed in its mounting with an O-ring and/or glue or other suitable adhesive such that no pressure can escape from a fluid side of the piston to an atmospheric side of the piston.

The hollow piston stem 600 is also provided with a longitudinal slot 650 running in a major part of the length of said hollow piston stem, but not extending to the piston portion. Said slot is arranged to make it possible for a slider of a sliding potentiometer 645 arranged inside said stem 600, to be mechanically connected to the syringe housing, preferably in the area of a finger flange of the syringe housing. The slider of the potentiometer 645 is provided with a short rod 647, said rod penetrates the slot 650 and is connected to the syringe housing by means of epoxy resin or other suitable means. The above arrangement provides a resistance value of the potentiometer 645 corresponding to the position of the piston relative to the syringe housing. In an alternate embodiment piston position is determined by means of magnetic sensors arranged at the piston stem and magnetic areas arranged at the housing. Preferably said magnetic areas are cast inside a plastic material of said housing. In order to prevent the piston stem from rotating relative to the housing, misaligning magnetic sensors and magnetic areas, said housing and said piston are oval.

The hollow piston stem 600, is further provided with accommodations for, and a small microcontroller 670 with analogue to digital conversion capabilities e.g. ATMEGA48V. Said microcontroller is connected to said pressure sensor and said potentiometer for processing of electrical signals representative of fluid pressure and of piston position making it possible to calculate fluid flow and fluid flow resistance as described above. Fluid pressure and piston position is measured 10 to 100 times a second and fluid flow resistance is calculated according to the formula (1) presented above. Signal processing includes compensating for flow values lagging a corresponding pressure value a small amount of time.

The hollow piston stem 600 is further provided with a radio communicating unit 680 for communicating pressure, flow and resistance values to a remote unit. In an alternate embodiment the communication is performed via a thin cable and there will be a cable interface unit instead of a radio communication unit.

Further, the hollow piston stem is provided with a power supply & power saving unit 690. The unit 690 preferably comprises a small high performance battery with suitable shape and dimensions for fitting into said stem 600. The power supply & power save unit is provided with means for cutting and restoring power in order to save power. Said unit 690 cuts power when a thumb rest of the syringe housing has not been pressed for a certain amount of time, e.g., 20 minutes. The power unit restores power when the thumb rest is pressed.

An advantage of using a measuring device almost identical to a standard syringe is that the man-machine interface will be very similar. The touch and feel when injecting a fluid will be identical or almost identical to a standard syringe. Since many surgeons make great use of their tactile sense during operations, it is an advantage to provide an appliance that do not distort the interactive feedback that is provided by touch and feel during surgery.

Pressure Indicator

In preferred embodiments the syringe may be provided with one or more pressure indicators for indicating to the surgeon if a suitable pressure is applied. In a preferred embodiment three light emitting diodes (LEDs) are arranged such that a first LED is arranged to shine when the pressure is below a suitable range. A second LED is arranged to shine when pressure is in a suitable range, and a third LED is arranged to shine when pressure is above said suitable range. In this way the surgeon can adjust pressure to produce good measuring conditions.

Methods

The system described above is used in methods for assessing different kinds of flow resistance and related values being of interest during coronary artery bypass grafting.

The output from the reading device, which can be read by the surgeon, will hence provide information that serves as an indication of occluding coronary competitive flow, run off quality in the coronary beds and flow resistance on the arrested heart. For a detailed explanation of these cardiology terms, see a modern cardiology textbook or the articles referred to in the background section. Flow and resistance may also be measured intraoperatively on the beating heart in the native coronary artery at the distal portion after the occlusion. When measuring on the beating heart the variables are affected by the myocardial resistance during systolic contraction. The difference between the measurement on the beating heart and on the arrested heart gives a value of the coronary flow reserve (CFR) in the native coronary. The difference is due to the fact that the arrested and hypothermic heart allows maximum vasodilatation and small myocardial resistance.

Important factors to understand and to consider during surgical treatment of coronary disease are the coronary blood supply, myocardial resistance, competitive flow and coronary flow profile. These are all factors or variables that could indicate a problem during surgery and a surgeon could hereby perform immediate revision, avert complications, and thereby ensure early graft patency if he or she were aware of abnormal values. The objective of the present invention is to help measuring these factors and to reveal whether the flow disturbance is related to the anastomotic region, myocardial resistance or vascular steal effect.

The coronary arteries lie on the surface of the heart, and small arteries penetrate into the cardiac muscle mass. Most of the venous blood flow from the myocardium of the left ventricle leaves by way of the coronary sinus. The heart's pattern of contraction and relaxation modulates its myocardial resistance and during systolic contraction, flow resistance is higher and less flow perfuses the myocardium. When the stenosis in the native coronary is less than 100%, flow into the target myocardium is supplied by two branches, each with its own pressure profile Pgraft and Pcoron. The coronary branch offers a shorter path to the root of the aorta. Therefore, the systolic pressure pulse will typically reach the graft's distal anastomosis, first via the native coronary artery branch, then via the graft branch. The influence of the competitive flow on graft flow depends on the magnitude of the resistances Rcoron and Rgraft. Rcoron is largely a function of the severity of the stenosis; Rgraft includes factors such as graft length and size, vasospasm, and technical errors.

Hence, a graft's capacity to deliver flow may be reduced by factors other than graft patency. One such factor is competitive flow which results when a partly stenosed native coronary continues to contribute flow. Since both the graft and the native coronary are supplying blood to the post-anastomotic segment, the full flow potential of the graft is not realized. To test a graft at its maximum flow capacity, the competitive flow from the native coronary artery could be blocked. Two measurements are necessary: one without manual occlusion and one with manual occlusion by snaring, finger pressure, forceps, or the like. Increase in graft flow with native coronary artery occlusion indicates the presence of competitive flow, and graft patency is best assessed with the occlusion applied.

An anastomosis can be technically perfect, but if there is high downstream resistance due to myocardial infarction and/or small vessel disease as seen in diabetics, flow will be relatively low. The lower contractility of diseased myocardium will alter the systolic/diastolic flow profile of the graft. This can be measured using the vascular resistance gauge according to an embodiment of the present invention.

Patent, functioning bypass grafts are fundamental to successful coronary artery bypass grafting (CABG), therefore intraoperative flow measurement on newly constructed bypass grafts sets the stage for this surgical success. The purpose of CABG surgery is to restore flow to the myocardium so that the heart can meet the body's metabolic demands.

When inadequate graft flow indicates a problem during surgery, a surgeon can perform immediate revision, avert complications, and thereby ensure early graft patency.

Today, intraoperative graft patency assessment methods vary, with transit-time ultrasound flowmetry as the most common technology.

The intention of graft patency determination is to understand the capability for uninhibited flow into the myocardium on the beating heart. The inventors realise that mean flow is the primary determinant of the quality of grafts. A high average flow always indicates a viable graft, and near-zero flow always indicates a graft in trouble. Mean flow alerts the surgeon to one of three graft conditions:

1. Mean flow falls within the normal range or above: the graft provides adequate flow and may be considered patent.

2. Mean flow below 5 ml/min: flow is unacceptably low; the graft is compromised and requires further examination.
3. Mean flow between 5 ml/min and normal range: further analysis must be performed to assess whether this graft performs acceptably

| Graft location | Normal flow range | Questionable flow | Obstructed flow |
| --- | --- | --- | --- |
| LIMA - LAD | 27 ml/min | 27 – 5 | 5 |
| RIMA - RCA | 26 | 26 – 5 | 5 |
| SVG - RCA | 29 | 29 – 5 | 5 |
| SVG - DIAG | 21 | 21 – 5 | 5 |
| SVG - OM1, OM2 | 29 | 29 – 5 | 5 |
| SVG - PDA | 24 | 24 – 5 | 5 |
| SCG - CX | 48 | 48 – 5 | 5 |

Ref: Typical mean flow readings in coronary grafts compiled from statistical averages of 589 transit-time flow measurements reported in the literature (Web site: www.transonic.com). LIMA = Left internal mammarian artery, LAD = Left anterior descending artery, RCA = Right coronary artery etc.

In order to improve the evaluation of graft function the present invention may be used in combination with transit time technology. One aim of the present invention is to measure the resistance to flow on the arrested heart. The measurement of coronary vascular resistance on the arrested heart (zero cardiac work) reveals an early warning on grafts and coronary beds at potential high risk for inadequate perfusion. This allows the surgeon to improve the graft function before going off the pump and to prepare for off pump and postoperative complications. The procedure according to the present invention is to slowly inject liquid through the vein graft by means of the special syringe provided with sensors. This could be done both by occluding the native coronary artery and without occluding the native coronary artery, in order to evaluate occluding competitive flow, run off quality in the coronary beds and finally the flow resistance. During injecting into the vein graft the intravascular pressure and flow is calculated from sensor data and presented on the reading device. The cardio vascular resistance (CVR) may be automatically presented on the display by applying Poiseuille-Hagen or other fluid mechanics equations. It is the experience of the inventor(s) that the mean CVR value should not exceed 3 mmHg/ml/min, to allow good perfusion of the cardiac muscle through the new grafting. Measuring resistance to flow on the arrested heart according to the present invention in combination with the transit time measurement on the beating heart gives a good combination of quality assurance of the graft patency determination.

There is a need for a method of graft patency verification to be used intraoperatively during surgical coronary revascularization. However, it is also recognized that coronary flow physiology is complex and physiological flow measurements depend on competitive flow in the native circulation. The physiology is further complicated by the fact that postoperative flow in saphenous vein grafts is different than flow in mammary and other arterial conduits. Flow measurements also change when arterial conduits are used as pedicles or are skeletonized. However, empirical experience has shown that the ability of surgeons to interpret flow parameters will improve in time. In this regard, surgeons will gain a better experience with issues regarding competitive flow and low flow, among other issues.

Therefore, a method and/or a device for intraoperatively, during surgical coronary revascularization, verifying graft patency is highly desirable.

Method for Measuring Free Graft Patency

During surgery, free graft patency is measured by the following method:
Providing the graft, e.g. by taking out the saphenous vein from one leg of the patient.
Preparing the vein for becoming a graft according to standard procedures,
Connecting a first end of the vein, the end that will become the proximal end of the final anastomosis, to the tubing of the syringe of the vascular resistance gauge.
Injecting a fluid through the graft by manually pressing the piston part of the syringe, thereby creating a flow through the graft and a pressure in the syringe.
Reading the vascular resistance of the graft on the display of the reading device.

Method for Measuring Vascular Resistance of Coronary Vessels of Beating Heart

During open heart surgery, the resistance of coronary vasculature of the beating heart distal to a certain point is measured by the following method:
Opening chest and expose the heart according to standard procedures.
Identifying the coronary artery of interest.
Identifying point of interest, i.e. the point on the coronary artery of interest, where the graft is to be connected/sutured.
On the beating heart, making an incision at the point of interest and, if necessary, take measures to avoid unnecessary bleeding. The incision can be made by the aid of a so called "beaver", and the opening can be trimmed by the aid of a so called coronary pair of scissors.
Connecting the coronary artery of interest, at the point of interest, to the tubing of the syringe of the vascular resistance gauge. This can be done by inserting the tube of the vascular resistance graft into the coronary and make a suture to seal the connection. As an alternative, a special coupling or connection may be used.
Injecting a fluid into the coronary artery of interest, at the point of interest, by manually pressing the piston part of the syringe, thereby creating a flow through the graft and a pressure in the syringe. The injection is preferably continued during at least three heart beats, enabling calculation of a good average resistance and enabling selective use of either peak values for systolic resistance or low values for diastolic values.
Reading the average resistance of the coronary vascular bed of interest on the display of the reading device.
The method may also include reading maximum and minimum resistance on the display of the reading device.

Method for Measuring Vascular Resistance of Coronary Vessels on the Arrested Heart During open heart surgery, the resistance of coronary vasculature of the arrested heart distal to a certain point is measured by a method comprising the following steps:
Opening chest and expose the heart according to standard procedures.
Identifying the coronary artery of interest.
Identifying point of interest, i.e. the point on the coronary artery of interest, where the graft is to be connected/sutured.
Preparing for arresting the heart.
Preparing for switching to heart-lung machine.
Arresting heart, switch to heart-lung machine.
Connecting the distal end of the graft to the native coronary
Connecting the proximal end of the coronary artery of interest, at the point of interest, to the tubing of syringe of the vascular resistance gauge.

On the arrested heart, injecting a fluid into the coronary artery of interest, at the point of interest, by manually pressing the piston part of the syringe, thereby creating a flow through the graft and a pressure in the syringe.

Reading the resistance value corresponding to the resistance of the combination of the graft and the native coronary on the display of the reading device.

Method for Estimating Coronary Flow Reserve of Coronary Vascular Bed

The coronary flow reserve CFR is defined as the coronary vascular resistance of the beating heart $CVR_1$ divided by the coronary vascular resistance of the arrested heart $CVR_0$ as expressed by formula (2).

$$CFR = \frac{CVR_1}{CVR_0} \quad (2)$$

Coronary flow reserve can be estimated by performing measurements according to the methods described above for CVR.sub.1 and CVR.sub.0 and subsequently dividing them.

Method for Estimating Steal Effect Due to Coronary Competitive Flow

A graft can make a more or less successful contribution to restoring coronary blood supply, and one of the parameters affecting the flow of the new branch is the occurrence of the so called steal phenomena. The steal phenomena is explained as blood that, instead of flowing the intended way, takes another way, for example flowing backwards in the native coronary vessel. A method for estimating the steal effect due to backflow in native coronary artery comprises the steps of the above described method of measuring vascular resistance of coronary vessels of a arrested and beating heart, respectively, but instead the connection of the tubing of the syringe of the vascular resistance gauge is done such that fluid is made to flow backwards in the (sometimes occluded) native artery. This can be done by occluding the native coronary, and then inject through the graft and the myocardium. Then injecting is performed with the native coronary open. The difference in resistance and flow when native coronary is occluded and not occluded demonstrates competitive flow and graft patency.

Method for Measuring Combined Graft, Sutured Joint and Native Vascular Resistance When the surgeon has sutured a distal end of the graft to the native coronary artery at a point distal to a stenosis forming a joint, it is desirable to measure a combined graft and native vascular resistance. This is preferably achieved by a method comprising the following steps:

Checking that the graft and the suture between the graft and the native artery are in satisfactory state.

Connecting the tube of the syringe of the vascular resistance gauge to the proximal end of the graft.

Injecting a fluid into the graft by manually pressing the piston part of the syringe, thereby creating a flow through the graft and the coronary artery and the vascular bed supplied from it, and a pressure.

Stent Control

Stent control refers to the activity of measuring the fraction between the values of post and prestenotic pressure, flow and resistance, and to compare these values before and after a stent implantation. The fraction gives the percentage of the pressure, flow and resistance through the stenosis related to the flow as if the vessel was healthy. By adding resistance to flow it's becoming a new absolute version of physiological method of measurement which makes it possible to determine the significance of the stenosis in terms of flow and resistance impairment. Intravascular pressure, flow and resistance measurement by stent control is also valuable after treatment in order to determine whether or not the intervention has been successful. According to the present invention a procedure is to measure pressure, flow and resistance at the proximal end of the balloon catheter by mounting the vascular resistance gauge syringe in a first balloon catheter's luer-lock connection. The balloon catheter is then inserted into the coronary vessel by means of standard Judkins technique, i.e. via an incision in one of the femoral arteries. The balloon is inflated just before the stenosis (prestenotic), and pressure and resistance values are measured. Subsequently, the balloon is deflated and advanced forward to just after the stenosis (poststenotic). The balloon is inflated again and sampling of pressure and resistance values is performed. The first balloon catheter is then removed. Then a stent is mounted on a second balloon catheter and after the balloon is inflated and the stent is implanted, a new measurement of pressure, flow and resistance is made through the proximal end of the stent balloon catheter. This procedure will give the user three set of values, one set that is prestenotic, one that is poststenotic and finally one set that gives the post implanted values.

The invention claimed is:

1. A system suitable for assessing vascular patency comprising a syringe with a piston part and a housing, for injecting a fluid into a vessel or a vascular graft, and means for sensing the pressure of the fluid in the syringe and means for determining a flow rate of said fluid, said piston part being arranged to be manually pressable, and said means for determining the flow rate comprising means for electrically or magnetically determining the rate of movement of the piston part of said syringe relative to the housing of said syringe when said piston part is manually pressed.

2. The system of claim 1 where said means for sensing the pressure of the fluid in the syringe comprises a pressure sensor, arranged at the piston part of the syringe and communicating with the pressure of the fluid in the syringe through a pressure channel, a first end of the pressure channel being arranged at a piston, being exposed to the pressure of the fluid in the syringe, and wherein the first end may be protected by a flexible membrane; the second end of the pressure channel being connected to the pressure sensor.

3. The system according to claim 1 or 2, where said syringe comprises a magnetic area arranged in mechanical contact with said piston part and where a magnetic sensor is arranged in mechanical contact with said syringe housing.

4. The system of claim 3, where a magnetic tape provided with alternatively magnetic and non-magnetic areas is attached to the piston part, and where two magnetic sensors are arranged on said syringe housing having a distance between said two magnetic sensors that is not a multiple of the distance between two magnetic areas of said magnetic tape.

5. The system of claim 1, where the position of said piston part is sensed by a capacitive circuit where the housing of the syringe is provided with conductive areas attached to the syringe housing and where also the piston part of said syringe is provided with conductive areas in such a way that when the piston part of said syringe is pressed into the housing of said syringe, a capacitance of an electrical circuit comprising both said conductive areas is changed.

6. The system of claim 1, where a stationary part of a potentiometer is attached to the syringe housing and a mobile part of said potentiometer is attached to the piston part of said syringe.

7. The system of claim 1, further comprising a reading device for use with the syringe, where said reading device comprises at least one inlet for signals representative of the position of said piston part and fluid pressure.

8. The system of claim 7, where said reading device further comprises a display and means for calculating a fluid flow value, selected from pressure and flow rate of the fluid, using said signals representative of said position of the piston part.

9. The system of claim 8, where said reading device further comprises means to compute a vascular resistance value from said pressure of the fluid and said position of the piston part signals.

10. The system of claim 9 for inter-operatively assessing vascular resistance, further comprising a tube for connecting the syringe to the said vessel or vascular graft, and a cable for connecting one or more sensors of the syringe to the reading device.

11. The system according to claim 1 or 2, where said syringe comprises a magnetic area arranged in mechanical contact with said syringe housing and where a magnetic sensor is arranged in mechanical contact with said piston part.

12. The system of claim 11, where a magnetic tape provided with alternatively magnetic and non-magnetic areas is attached to said syringe housing, and where two magnetic sensors are arranged on said piston part having a distance between said two magnetic sensors that is not a multiple of the distance between two magnetic areas of said magnetic tape.

13. The system of claim 1, where a stationary part of a potentiometer is attached to the piston part of said syringe and a mobile part of said potentiometer is attached to the syringe housing.

* * * * *